(12) United States Patent
Kane et al.

(10) Patent No.: US 7,560,598 B2
(45) Date of Patent: Jul. 14, 2009

(54) FRAGRANCE COMPOSITIONS FROM TERTIARY TERPENE ALCOHOLS

(75) Inventors: Bernard J. Kane, Atlantic Beach, FL (US); Mark B. Erman, Atlantic Beach, FL (US)

(73) Assignee: Millennium Specialty Chemicals, Inc., Houston, TX (US)

( * ) Notice: Subject to any disclaimer, the term of this patent is extended or adjusted under 35 U.S.C. 154(b) by 628 days.

(21) Appl. No.: 11/400,270

(22) Filed: Apr. 7, 2006

(65) Prior Publication Data

US 2007/0238629 A1    Oct. 11, 2007

(51) Int. Cl.
*C07C 45/00* (2006.01)
*C07D 323/02* (2006.01)
*A61K 8/18* (2006.01)

(52) U.S. Cl. .................. 568/403; 568/407; 549/346; 549/430; 512/11

(58) Field of Classification Search .......... 568/403, 568/407; 549/346, 430; 512/11
See application file for complete search history.

(56) References Cited

U.S. PATENT DOCUMENTS

| | | | |
|---|---|---|---|
| 2,824,138 A | 2/1958 | Wystrach et al. | 260/586 |
| 3,030,337 A | 4/1962 | Hedrick | 260/63 |
| 3,361,820 A | 1/1968 | White et al. | 260/586 |
| 3,481,998 A | 12/1969 | Gibson et al. | 260/675.5 |
| 3,658,851 A | 4/1972 | Gibson et al. | 260/346.2 |
| 4,048,120 A | 9/1977 | Rautenstrauch | 512/8 |

OTHER PUBLICATIONS

Le-Van-Thoi, "Pinonic Acid and Its Derivatives" *Ann. Chim*, vol. 10, 1955, pp. 35-54. Beilstein Institute for Organic Chemistry, Frankfurt-Main, DE, XP002447554.
Le-Van-Thoi, "Pinonic Acid and Its Derivatives" *Ann. Chim*, vol. 10, 1955, pp. 35-54. Beilstein Institute for Organic Chemistry, Frankfurt-Main, DE, XP002447555.
Lui, Fu-Chu et al., "Syntheses and Stereochemistry of Tetrahydrofuran Derivatives from Alpha-Pinene", *Org. Prep. Proced. Inc.*, vol. 29, No. 4, 1997, pp. 473-476. Beilstein Institute for Organic Chemistry, Frankfurt-Main, DE, XP002447556.
Th. Kaufmann, et al., "Cyano(methyl)argentate: Spektroskopie, Selektivität als Methylierungsreagentien, Vergleich mit anderen Methylsilber-Reagenzien", *Chem. Ber.*, vol. 125, 1992, pp. 2409-2418, XP002447549, p. 2413, scheme 2, compound 14; p. 2417, paragraph 5.
G.A. Schmidt et al., Terpene Hydroperoxides. IV. The Thermal Decomposition of Pinane Hydroperoxide. *JACS*, vol. 81, 1959, p. 448, XP002447550 figure 2, compounds IV and XII.
T. Gibson et al., *Tetrahedron Lett. 10* (1967) 905.
T. Gibson et al., *J. Am. Chem. Soc. 97* (1969) 4771.
P. Hobbs et al., *J. Am. Chem. Soc. 98* (1976) 4594.
N. Bosworth et al., *J. Chem. Soc., Perkin Trans. 1* (1972) 943.
H. Lempers et al., *Chem. Lett.* (2002) 830.

*Primary Examiner*—Sikarl A Witherspoon
(74) *Attorney, Agent, or Firm*—Jonathan L. Schuchardt

(57) ABSTRACT

Cyclic ethers or chloroketones useful as fragrance components or intermediates are made by reacting a saturated, tertiary terpene alcohol with hypochloric acid under conditions effective to promote oxidation. trans-Pinanol gives predominantly 6,9-dimethyl-7-oxatricyclo[4.3.0.0$^{3,9}$]-nonane, while cis-pinanol yields almost exclusively 1-acetyl-3-(2-chloroethyl)-2,2-dimethylcyclobutane, a new and versatile intermediate for making cyclobutane derivatives having interesting and diverse aromas.

12 Claims, No Drawings

FRAGRANCE COMPOSITIONS FROM TERTIARY TERPENE ALCOHOLS

FIELD OF THE INVENTION

The invention relates to a process for making cyclic ethers and chloroketones from tertiary terpene alcohols. The products are valuable intermediates for new fragrance compositions.

BACKGROUND OF THE INVENTION

Terpenes are ubiquitous starting materials for synthesizing fragrance ingredients. Saturated, tertiary terpene alcohols, which derive from turpentines and incorporate 2-methylbutane moieties, are important fragrance ingredients or intermediates because of their availability and relatively low cost. These alcohols include trans-pinanol, cis-pinanol, dihydroplinol, tetrahydromyrcenol, tetrahydrolinalool, and other valuable compounds. Cis-pinanol, for example, is commonly pyrolyzed to make industrial quantities of linalool.

Oxidation of trans-pinanol with mercury(II) oxide and bromine or with lead tetraacetate and iodine provides 6,9-dimethyl-7-oxatricyclo[4.3.0.0$^{3,9}$]nonane, compound 1, a valuable intermediate for synthesizing more complex terpene derivatives (see, e.g., U.S. Pat. Nos. 3,481,998 and 3,658,851; *Tetrahedron Lett.* (1967) 905; *J. Am. Chem. Soc.* 97 (1969) 4771 and 98 (1976) 4594; and *J. Chem. Soc., Perkin Trans. I* (1972) 943). More recently, cyclic ether 1 has also been made by dehydrating trans-pinane hydroperoxide with a mixture of iron(II) and copper(II) sulfates (*Chem. Lett.* (2002) 830), as shown below. While the methods are effective, a preferred one would avoid the need to make a hydroperoxide intermediate or to use toxic lead or mercury reagents.

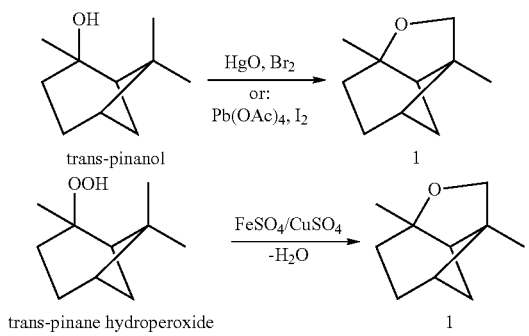

A number of cyclobutanes have been identified as valuable fragrance components. Unfortunately, synthesizing cyclobutanes is usually far from trivial, particularly if the starting materials are limited to readily available, inexpensive mixtures such as terpenes. Despite the challenges, cyclobutanes such as pinonyl alcohol, pinonic acid, and esters of pinonic acid have been reported (see U.S. Pat. Nos. 2,824,138, 3,030,337, 3,361,820, and 4,048,120). Surprisingly little progress has been made during the past thirty years to develop new terpene-based routes to cyclobutanes.

SUMMARY OF THE INVENTION

In one aspect, the invention is an oxidation process. We found that certain chloroketones, cyclic ethers, or mixtures thereof can be made by reacting a saturated, tertiary terpene alcohol with hypochloric acid under conditions effective to promote the oxidation. Under these conditions, trans-pinanol provides predominantly 6,9-dimethyl-7-oxatricyclo[4.3.0.0$^{3,9}$]nonane. Interestingly, oxidation of cis-pinanol with hypochloric acid provides previously unknown 1-acetyl-3-(2-chloroethyl)-2,2-dimethylcyclobutane, 2:

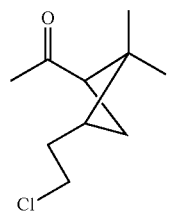

2

Chloroketone 2 is exceptionally versatile; we readily converted it to a host of new cyclobutane derivatives having interesting and diverse aromas. Thus, in addition to the oxidation process, the invention includes chloroketone and cyclobutane compositions, and fragrances comprising the cyclobutanes.

DETAILED DESCRIPTION OF THE INVENTION

Cyclic ethers or chloroketones useful as fragrance components or intermediates are made by reacting a saturated, tertiary terpene alcohol with hypochloric acid under conditions effective to promote oxidation.

Suitable saturated, tertiary terpene alcohols comprise 2-methylbutane subunits, at least one tertiary hydroxyl group, and no carbon-carbon double bonds. The alcohols can, and often do, have one or more carbocyclic rings. The terpene alcohols can be synthesized, or they can be isolated from natural sources. Usually, they are synthesized from pinenes or other terpene-rich mixtures. Preferred terpene alcohols include, for example, cis-pinanol, trans-pinanol, dihydroplinol, tetrahydromyrcenol, tetrahydrolinalool, 2-methylisoborneol, 1,3,3- trimethylcyclohexanol, hexahydronerolidol, tetrahydrobisabolol, tetrahydromanool, and mixtures thereof, which have the structures indicated below. Any of the stereoisomers of these compounds can be used. The general structures of some preferred saturated, tertiary terpene alcohols appear below:

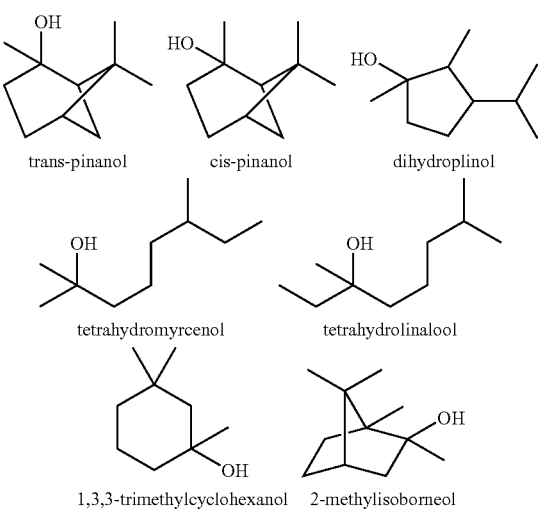

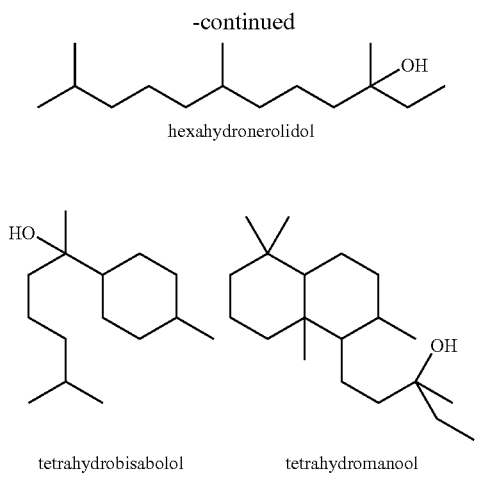

hexahydronerolidol tetrahydrobisabolol    tetrahydromanool

The oxidation process is performed in the presence of hypochloric acid (HOCl). Hypochloric acid is typically generated by carefully acidifying an aqueous hypochlorite solution or suspension with an organic or mineral acid. We found it particularly convenient to generate hypochloric acid in situ by passing gaseous carbon dioxide through an aqueous solution or suspension of an alkali metal hypochlorite (e.g., sodium hypochlorite) or an alkaline earth metal hypochlorite (see Examples 1-4, below). Aqueous sodium hypochlorite is readily available as a 5-6% active NaOCl solution in commercial bleach, e.g., Chlorox® bleach.

The process is performed under conditions effective to promote oxidation of the terpene alcohol to a cyclic ether, a chloroketone, or a mixture thereof. The oxidation usually proceeds readily under mild conditions of temperature and pressure. For exothermic reactions, cooling can be applied if desired to help control the reaction rate. Often, the heat of reaction is effective in warming the reaction to a desirable temperature. Generally, the oxidation process is performed at a temperature within the range of about 0° C. to about 150° C., more preferably from about 20° C to about 100° C., most preferably from about 30° C. to about 80° C. While the reaction can be performed at, above, or below atmospheric pressure, it is usually most convenient to use atmospheric pressure.

The exact nature of the product or product mixture will depend on many factors, including temperature, pressure, solvent selection (if any), the relative amounts of terpene alcohol and hypochloric acid, and other factors. The exact products and product ratios usually depend principally on the identity of the terpene alcohol. Sometimes, the process provides a single product type. For instance, selection of cis-pinanol as the terpene alcohol provides only 1-acetyl-3-(2-chloroethyl)-2,2-dimethylcyclobutane (chloroketone 2). Under some conditions, a mixture of product types is obtained, as when trans-pinanol is oxidized to give a mixture of mostly 6,9-dimethyl-7-oxatricyclo[4.3.0.0$^{3,9}$]nonane (cyclic ether 1) plus a minor proportion of chloroketone 2. Oxidation of dihydroplinol provides principally 6-chloro-5-(1-methylethyl)-2-heptanone, a new chloroketone (3), while tetrahydromyrcenol gives mostly 2,2-dimethyl-5-(1-methylpropyl)tetrahydrofuran, 4:

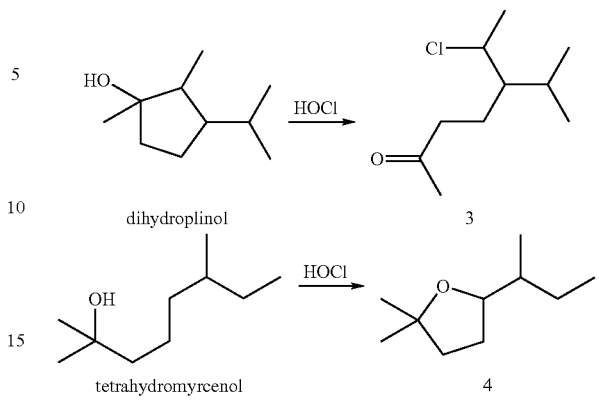

dihydroplinol    3 tetrahydromyrcenol    4

Oxidation of 2-methylisoborneol, 1,3,3-trimethylcyclohexanol, hexahydronerolidol, tetrahydrobisabolol, or tetrahydromanool should provide the corresponding cyclic ethers, each incorporating a tetrahydrofuranyl moiety. For example, the reaction of 1,3,3-trimethylcyclohexanol with HOCl should give a bicyclic ether:

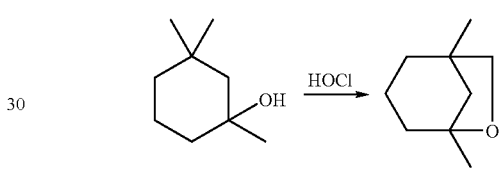

Chloroketones made by the process of the invention, by virtue of chloro and carbonyl functional groups, are exceptionally versatile. We demonstrated this versatility by elaborating chloroketone 2 to a host of potentially valuable cyclobutane derivatives (see Examples 5-17 below). Similar methodologies can be used to produce derivatives of other chloroketones available from the process such as 3.

The invention includes new chloroketones made by the process. The chloroketones are valuable intermediates for synthesizing fragrance components. In particular, the new chloroketones include compositions comprising at least one stereoisomer of 6-chloro-5-(1-methylethyl)-2-heptanone (3) or compositions comprising at least one stereoisomer of 1-acetyl-3-(2-chloroethyl)-2,2-dimethylcyclobutane (2).

The invention includes cyclobutanes derived from 2, excluding 1-acetyl-2,2-dimethyl-3-ethylcyclobutane, pinonyl alcohol, pinonic acid, and esters of pinonic acid, which are already known compounds.

Preferred cyclobutanes of the invention have the general structure:

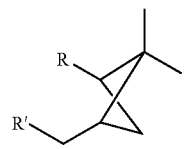

R is a monovalent substituent selected from the group consisting of $Me_2C(OH)$—, MeCO—, $CH_2$=CH—CMe(OH)—, $CH_2$=CMe—, and 2-methyl-1,3-dioxolan-2-yl. R' is a monovalent substituent selected from the group consisting of ClCH$_2$—, Me—, MeOCH$_2$—, EtOCH$_2$—, MeCH(OH)CH$_2$—, Me$_2$C(OH)CH$_2$—, and MeC(O)CH$_2$—.

The cyclobutanes are made from 2 using well-known synthetic methods (see Examples 5-17, below). As Table 1 demonstrates, the cyclobutanes have interesting and diverse aromas, making them potentially valuable for fragrance compositions. Thus, the invention includes fragrance compositions comprising at least one cyclobutane of the invention.

The following examples merely illustrate the invention. Those skilled in the art will recognize many variations that are within the spirit of the invention and scope of the claims.

EXAMPLE 1

Cyclic Ether 1

Carbon dioxide is bubbled through a stirred, warmed (~35° C.) mixture of trans-pinanol (600 g) and aqueous sodium hypochlorite (Chloroxe bleach® 5-6% active NaOCl, 6000 g) until gas chromatography (GC) analysis shows over 70% conversion of trans-pinanol. The layers are separated and the aqueous layer is extracted with heptane. The heptane extract is combined with the primary organic layer, and heptane is removed under vacuum. Aqueous sodium hydroxide (350 g of 25% NaOH) is added to the crude cyclic ether, and the mixture is cohobated for about 12 h. After cooling to ambient temperature, the contents of the flask and cohobation trap are poured into a separatory funnel. The organic layer is separated and distilled under vacuum (about 100 mm) to give purified cyclic ether 1 (b.p. about 115° C./100 mm; 329 g, 56% based on the charged amount of trans-pinanol). The structure of the product is confirmed by its spectral data (NMR, IR, GC/MS). The distillation also affords recovered trans-pinanol (b.p. about 135° C/100 mm, ~130 g). The yield of cyclic ether 1 based on reacted trans-pinanol is about 71%. GC analysis of the distillation residue also shows the presence of some chloroketone 2.

EXAMPLE 2

Chloroketone 2

Carbon dioxide is bubbled through a stirred mixture of cis-pinanol (300 g), heptane (120 mL), and aqueous sodium hypochlorite (3200 mL). The reaction is somewhat exothermic, so some cooling (water bath) is applied initially to keep the temperature at or below about 35° C. After the reaction is reasonably complete by GC (6-8 h, about 80% conversion), the organic layer is separated, washed with water, and dried over sodium sulfate. The reaction is repeated three more times, and all of the crude products are combined. After heptane is removed, the remaining material is rapidly distilled under vacuum to give a mixture containing chloroketone 2 (1235 g, about 88% by GC) and unreacted cis-pinanol (99 g, about 8%). The yield of 2 is 74% based on charged cis-pinanol, or 80% based on reacted cis-pinanol. Chloroketone 2 is further purified by fractional distillation (b.p. 86-90° C./1 mm) and its structure is confirmed using spectral data.

EXAMPLE 3

Chloroketone 3

Carbon dioxide is bubbled through a stirred mixture of dihydroplinol (25 g) and aqueous sodium hypochlorite (250 g). The reaction is slightly exothermic and warms by itself to 39-42° C. After 5 h, layers are separated, and the oil is cohobated with dilute aqueous NaHCO$_3$ (500 mL). The cohobate (21.8 g) contains, according to GC, 28.3% (6.2 g) of unreacted dihydroplinol and 52.2% (13.4 g) of chloroketone 3. The yield of 3 is 44% based on charged dihydroplinol and 58% based on reacted dihydroplinol. Pure chloroketone 3 is isolated from the cohobate by distillation using a Vigreux column, and its structure is confirmed from spectral data.

EXAMPLE 4

Cyclic Ether 4

Carbon dioxide is bubbled over 4 h at 43-52° C. through a stirred mixture of tetrahydromyrcenol (200 g) and aqueous sodium hypochlorite. After cooling to room temperature, the layers are separated, and the oil layer is cohobated with dilute aqueous NaHCO$_3$ (2000 g). According to GC, the cohobate (169 g) contains 42.5% (71.8 g) of unreacted tetrahydromyrcenol and 31.0% (52.4 g) of cyclic ether 4. The yield of 4 is 27% based on charged tetrahydromyrcenol and 41% based on reacted tetrahydromyrcenol. After purification by distillation and column chromatography, the structure of cyclic ether 4 is confirmed from spectral data.

EXAMPLES 5-17

Cyclobutane Derivatives 5-17

Cyclobutane derivatives 5-17, illustrated schematically below, are obtained by the following well-known methods using chloroketone 2 as the starting material. In all cases, the structures are confirmed using spectral data (NMR, IR, GC/MS).

Alkoxy derivatives 5, 6, and 8 are obtained from the corresponding chlorides by reacting them with ethanol or methanol in the presence of 50% NaOH and a phase-transfer catalyst (triethylbutylammonium chloride).

Chloroketal 7 is obtained by reacting chloroketone 2 with ethylene glycol catalyzed by p-toluenesulfonic acid.

Ketal 9 is obtained by reacting 7 with magnesium metal and decomposing the resulting Grignard reagent with ethanol/water.

Ketone 10, the only previously known compound among compounds 5-17, is obtained by acid-catalyzed deacetalization of 9.

Vinyl alcohols 11 and 12 are obtained by addition of vinylmagnesium bromide to the corresponding ketones 10 and 2.

Chloroalcohol 13 is synthesized by addition of methylmagnesium bromide to chloroketone 2.

Alkenyl chloride 14 is obtained by KHSO$_4$-catalyzed dehydration of alcohol 13.

Secondary alcohol 15 is obtained by reacting a Grignard reagent made from chloride 14 with acetaldehyde.

Ketone 16 is obtained by chromic acid oxidation of alcohol 15.

Hydroxyketal 17 is obtained by reacting a Grignard reagent from chloroketal 7 with acetone followed by workup with dilute aqueous acid.

Cyclobutane Derivatives 5-17
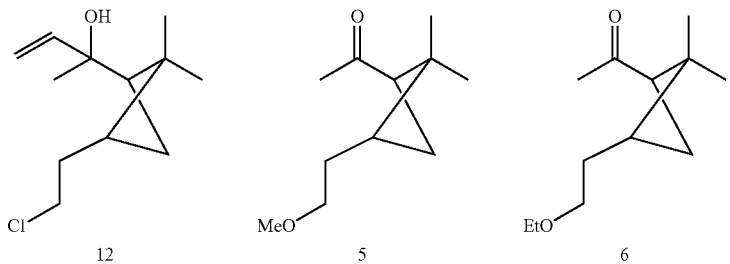
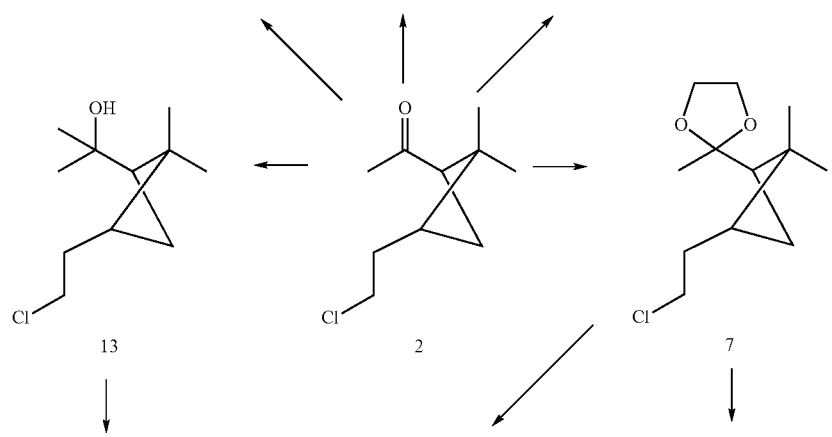
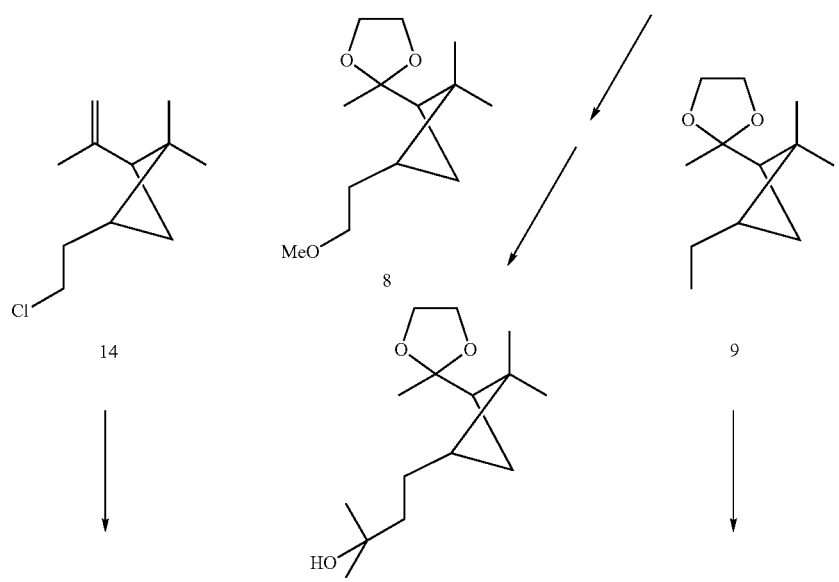

-continued

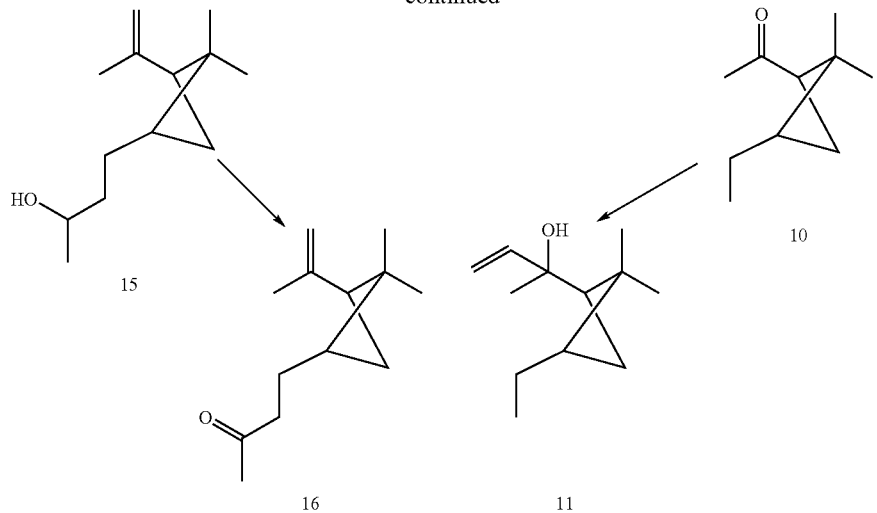

TABLE 1

Odor Characteristics of Cyclobutane Derivatives 5-12 and 15-17.

| Compound | Odor |
|---|---|
| Methoxyketone 5 | Woody floral with Ionone character, jasmine backnote |
| Ethoxyketone 6 | Similar to 5, but with some fresh fruity lavender flower note |
| Chloroketal 7 | Green, rosy, with slight shade of mushrooms |
| Methoxyketal 8 | Practically odorless |
| Ketal 9 | Fresh, camphoraceous, minty |
| Ketone 10 | Powerful thujone-like note with spicy background |
| Alcohol 11 | Powerful amber, fresh-diffusive-top-woody |
| Alcohol 12 | Weak, sour-metallic |
| Alcohol 15 | Fresh, fruity, lavender |
| Ketone 16 | Weak herbaceous, with a note of lavender, dry leaves |
| Hydroxyketal 17 | Weak woody |

The examples are meant only as illustrations. The following claims define the invention.

We claim:

1. A process which comprises reacting a saturated, tertiary terpene alcohol with hypochloric acid under conditions effective to produce at least one oxidation product selected from the group consisting of cyclic ethers, chloroketones, and mixtures thereof.

2. The process of claim 1 wherein the terpene alcohol is selected from the group consisting of cis-pinanol, trans-pinanol, dihydroplinol, tetrahydromyrcenol, tetrahydrolinalool, 2-methylisoborneol, 1,3,3-trimethylcyclohexanol, hexahydronerolidol, tetrahydrobisabolol, tetrahydromanool, and mixtures thereof.

3. The process of claim 1 wherein the terpene alcohol is cis-pinanol and the oxidation product comprises at least one stereoisomer of 1-acetyl-3-(2-chloroethyl)-2,2-dimethylcyclobutane.

4. The process of claim 1 wherein the terpene alcohol is trans-pinanol and the oxidation product comprises at least one stereoisomer of 6,9-dimethyl-7-oxatricyclo[4.3.0.0$^{3,9}$] nonane.

5. The process of claim 1 wherein the terpene alcohol is dihydroplinol and the oxidation product comprises at least one stereoisomer of 6-chloro-5-(1-methylethyl)-2-heptanone.

6. The process of claim 1 wherein the terpene alcohol is tetrahydromyrcenol and the oxidation product comprises at least one stereoisomer of 2,2-dimethyl-5-(1-methylpropyl) tetrahydrofuran.

7. The process of claim 1 wherein the hypochloric acid is generated in situ.

8. The process of claim 7 wherein the hypochloric acid is generated by passing carbon dioxide through an aqueous solution or suspension of an alkali metal hypochlorite or alkaline earth metal hypochlorite.

9. A composition comprising at least one stereoisomer of 6-chloro-5-(1-methylethyl)-2-heptanone.

10. A composition comprising at least one stereoisomer of 1-acetyl-3-(2-chloroethyl)-2,2-dimethylcyclobutane.

11. A cyclobutane having the general structure:

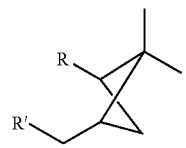

wherein

R is a monovalent substituent selected from the group consisting of $Me_2C(OH)$—, $MeCO$—, $CH_2$=CH—$CMe(OH)$—, $CH_2$=$CMe$—, and 2-methyl-1,3-dioxolan-2-yl; and R' is a monovalent substituent selected from the group consisting of $ClCH_2$—, Me—, $MeOCH_2$—, $EtOCH_2$—, $MeCH(OH)CH_2$—, $Me_2C(OH)CH_2$—, and $MeC(O)CH_2$— excluding 1-acetyl-2,2-dimethyl-3-ethylcyclobutane.

12. A fragrance comprising at least one cyclobutane of claim 11.

* * * * *